(12) United States Patent
Kshirsagar et al.

(10) Patent No.: US 8,476,292 B2
(45) Date of Patent: *Jul. 2, 2013

(54) AMIDE AND CARBAMATE DERIVATIVES OF N-{2-[4-AMINO-2-(ETHOXYMETHYL)-1H-IMIDAZO[4,5-C]QUINOLIN-1-YL]-1,1-DIMETHYLETHYL} METHANESULFONAMIDE AND METHODS

(75) Inventors: Tushar A. Kshirsagar, Woodbury, MN (US); Shri Niwas, Maple Grove, MN (US); Bryon A. Merrill, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 845 days.

This patent is subject to a terminal disclaimer.

(21) Appl. No.: 11/991,663

(22) PCT Filed: Sep. 8, 2006

(86) PCT No.: PCT/US2006/035179
§ 371 (c)(1),
(2), (4) Date: Aug. 24, 2010

(87) PCT Pub. No.: WO2007/030775
PCT Pub. Date: Mar. 15, 2007

(65) Prior Publication Data
US 2010/0317684 A1    Dec. 16, 2010

Related U.S. Application Data

(60) Provisional application No. 60/715,950, filed on Sep. 9, 2005.

(51) Int. Cl.
*A61K 31/437* (2006.01)
*C07D 471/04* (2006.01)
*C07D 471/06* (2006.01)

(52) U.S. Cl.
USPC ............................................ 514/290; 546/81

(58) Field of Classification Search
USPC ............................................ 546/81; 514/290
See application file for complete search history.

(56) References Cited

U.S. PATENT DOCUMENTS

| | | | |
|---|---|---|---|
| 3,314,941 A | 4/1967 | Littell et al. | |
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gester | |
| 5,346,905 A | 9/1994 | Gerster | |
| 5,352,784 A | 10/1994 | Nikolaides et al. | |
| 5,367,076 A | 11/1994 | Gerster | |
| 5,389,640 A | 2/1995 | Gerster et al. | |
| 5,395,937 A | 3/1995 | Nikolaides et al. | |
| 5,444,065 A | 8/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,525,612 A | 6/1996 | Gerster | |
| 5,627,281 A | 5/1997 | Nikolaides et al. | |
| 5,644,063 A | 7/1997 | Lindstrom et al. | |
| 5,648,516 A | 7/1997 | Nikolaides et al. | |
| 5,684,018 A * | 11/1997 | Alexander | 514/316 |
| 5,693,811 A | 12/1997 | Lindstrom | |
| 5,714,608 A | 2/1998 | Gerster | |
| 5,741,908 A | 4/1998 | Gerster et al. | |
| 5,756,747 A | 5/1998 | Gerster et al. | |
| 5,886,006 A | 3/1999 | Nikolaides et al. | |
| 5,939,090 A | 8/1999 | Beaurline et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,200,592 B1 | 3/2001 | Tomai et al. | |
| 6,245,776 B1 | 6/2001 | Skwierczynski et al. | |
| 6,331,539 B1 | 12/2001 | Crooks et al. | |
| 6,365,166 B2 | 4/2002 | Beaurline et al. | |
| 6,376,669 B1 | 4/2002 | Rice et al. | |
| 6,440,992 B1 | 8/2002 | Gerster et al. | |
| 6,451,810 B1 | 9/2002 | Coleman et al. | |
| 6,486,168 B1 | 11/2002 | Skwierczynski et al. | |
| 6,514,985 B1 | 2/2003 | Gerster et al. | |

(Continued)

FOREIGN PATENT DOCUMENTS

| EP | 0 394 026 | 10/1990 |
|---|---|---|
| EP | 1 104 764 | 6/2001 |

(Continued)

OTHER PUBLICATIONS

Krise Jeffrey et al , 2005.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Caplus, English Abstract DN 139:929. Gorden Keith et al., Toll-like receptors teaches similar compounds, see RN 532959-63-0. Again they read on the compounds wherein NH-Y-R group is an NH2. The—Y-R group makes the compounds the prodrugs of the prior art compounds.
Testerman et al., Cytokine induction by the immunomodulators imiquimod and S-27609. J Leukoc Biol. 1995 Sep;58(3):365-72.

(Continued)

Primary Examiner — Rita Desai

(57) ABSTRACT

Amide and carbamate derivatives N-{2-[4-amino-2-(ethoxymethyl)-1H-imidazo[4,5-c]quinolin-1-yl]-1,1-dimethylethyl}methanesulfonamide, pharmaceutical compositions containing these compounds, methods of making the compounds, and methods of use of these compounds in modulating the immune system, for inducing cytokine biosynthesis in animals and in the treatment of diseases including viral and neoplastic diseases, are disclosed.

13 Claims, No Drawings

U.S. PATENT DOCUMENTS

| | | | |
|---|---|---|---|
| 6,518,265 B1 | 2/2003 | Kato et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,610,319 B2 | 8/2003 | Tomai et al. | |
| 6,627,638 B2 | 9/2003 | Gerster et al. | |
| 6,627,640 B2 | 9/2003 | Gerster et al. | |
| 6,630,588 B2 | 10/2003 | Rice et al. | |
| 6,638,944 B2 | 10/2003 | Mickelson | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,696,076 B2 | 2/2004 | Tomai et al. | |
| 6,696,465 B2 | 2/2004 | Dellaria et al. | |
| 6,703,402 B2 | 3/2004 | Gerster et al. | |
| 6,706,728 B2 | 3/2004 | Hedenstrom et al. | |
| 6,716,988 B2 | 4/2004 | Dellaria et al. | |
| 6,720,333 B2 | 4/2004 | Dellaria et al. | |
| 6,720,334 B2 | 4/2004 | Dellaria et al. | |
| 6,720,422 B2 | 4/2004 | Dellaria et al. | |
| 6,743,920 B2 | 6/2004 | Lindstrom et al. | |
| 6,756,382 B2 | 6/2004 | Coleman et al. | |
| 6,797,718 B2 | 9/2004 | Dellaria et al. | |
| 6,800,624 B2 | 10/2004 | Crooks et al. | |
| 6,809,203 B2 | 10/2004 | Gerster et al. | |
| 6,818,650 B2 | 11/2004 | Griesgraber | |
| 6,825,350 B2 | 11/2004 | Crooks et al. | |
| 6,841,678 B2 | 1/2005 | Merli et al. | |
| 6,852,861 B2 | 2/2005 | Merli et al. | |
| 6,878,719 B2 | 4/2005 | Lindstrom et al. | |
| 6,888,000 B2 | 5/2005 | Crooks et al. | |
| 6,894,060 B2 | 5/2005 | Slade | |
| 6,894,165 B2 | 5/2005 | Gerster et al. | |
| 6,897,221 B2 | 5/2005 | Crooks et al. | |
| 6,903,113 B2 | 6/2005 | Heppner et al. | |
| 6,916,925 B1 | 7/2005 | Rice et al. | |
| 6,921,826 B2 | 7/2005 | Dellaria et al. | |
| 6,924,293 B2 | 8/2005 | Lindstrom | |
| 6,943,225 B2 | 9/2005 | Lee et al. | |
| 6,949,649 B2 | 9/2005 | Bonk et al. | |
| 6,953,804 B2 | 10/2005 | Dellaria et al. | |
| 6,969,722 B2 | 11/2005 | Heppner et al. | |
| 6,989,389 B2 | 1/2006 | Heppner et al. | |
| 7,030,129 B2 | 4/2006 | Miller et al. | |
| 7,030,131 B2 | 4/2006 | Crooks et al. | |
| 7,038,053 B2 | 5/2006 | Lindstrom et al. | |
| 7,049,439 B2 | 5/2006 | Crooks et al. | |
| 7,078,523 B2 | 7/2006 | Crooks et al. | |
| 7,091,214 B2 | 8/2006 | Hays et al. | |
| 7,098,221 B2 | 8/2006 | Heppner et al. | |
| 7,112,677 B2 | 9/2006 | Griesgraber | |
| 7,115,622 B2 | 10/2006 | Crooks et al. | |
| 7,125,890 B2 | 10/2006 | Dellaria et al. | |
| 7,132,429 B2 | 11/2006 | Griesgraber et al. | |
| 7,132,438 B2 | 11/2006 | Frenkel et al. | |
| 7,148,232 B2 | 12/2006 | Gerster et al. | |
| 7,157,453 B2 | 1/2007 | Crooks et al. | |
| 7,163,947 B2 | 1/2007 | Griesgraber et al. | |
| 7,179,253 B2 | 2/2007 | Graham et al. | |
| 7,199,131 B2 | 4/2007 | Lindstrom | |
| 7,214,675 B2 | 5/2007 | Griesgraber | |
| 7,220,758 B2 | 5/2007 | Dellaria et al. | |
| 7,226,928 B2 | 6/2007 | Mitra et al. | |
| 7,276,515 B2 | 10/2007 | Dellaria et al. | |
| 7,288,550 B2 | 10/2007 | Dellaria et al. | |
| 7,301,027 B2 | 11/2007 | Colombo et al. | |
| 7,375,180 B2 | 5/2008 | Gorden et al. | |
| 7,387,271 B2 | 6/2008 | Noelle et al. | |
| 7,393,859 B2 | 7/2008 | Coleman et al. | |
| 7,427,629 B2 | 9/2008 | Kedl et al. | |
| 7,485,432 B2 | 2/2009 | Fink et al. | |
| 7,544,697 B2 | 6/2009 | Hays et al. | |
| 7,576,068 B2 | 8/2009 | Averett | |
| 7,578,170 B2 | 8/2009 | Mayer et al. | |
| 7,579,359 B2 | 8/2009 | Krepski et al. | |
| 7,598,382 B2 | 10/2009 | Hays et al. | |
| 7,612,083 B2 | 11/2009 | Griesgraber | |
| 7,648,997 B2 | 1/2010 | Kshirsagar et al. | |
| 7,655,672 B2 | 2/2010 | Statham et al. | |
| 7,687,628 B2 | 3/2010 | Gutman et al. | |
| 7,696,159 B2 | 4/2010 | Owens et al. | |
| 7,699,057 B2 | 4/2010 | Miller et al. | |
| 7,731,967 B2 | 6/2010 | O'Hagan et al. | |
| 7,799,800 B2 | 9/2010 | Wightman | |
| 7,879,849 B2 | 2/2011 | Hays et al. | |
| 7,884,207 B2 | 2/2011 | Stoermer et al. | |
| 7,888,349 B2 | 2/2011 | Kshirsagar et al. | |
| 7,897,597 B2 | 3/2011 | Lindstrom et al. | |
| 7,897,609 B2 | 3/2011 | Niwas et al. | |
| 7,897,767 B2 | 3/2011 | Kshirsagar et al. | |
| 7,902,209 B2 | 3/2011 | Statham et al. | |
| 7,902,210 B2 | 3/2011 | Statham et al. | |
| 7,902,211 B2 | 3/2011 | Statham et al. | |
| 7,902,212 B2 | 3/2011 | Statham et al. | |
| 7,902,213 B2 | 3/2011 | Statham et al. | |
| 7,902,214 B2 | 3/2011 | Statham et al. | |
| 7,902,215 B2 | 3/2011 | Statham et al. | |
| 7,902,216 B2 | 3/2011 | Statham et al. | |
| 7,902,242 B2 | 3/2011 | Statham et al. | |
| 7,902,243 B2 | 3/2011 | Statham et al. | |
| 7,902,244 B2 | 3/2011 | Statham et al. | |
| 7,902,245 B2 | 3/2011 | Statham et al. | |
| 7,902,246 B2 | 3/2011 | Statham et al. | |
| 7,906,506 B2 | 3/2011 | Griesgraber et al. | |
| 7,915,281 B2 | 3/2011 | Moser et al. | |
| 7,939,526 B2 | 5/2011 | Radmer et al. | |
| 7,943,609 B2 | 5/2011 | Griesgraber et al. | |
| 7,968,562 B2 | 6/2011 | Skwierczynski et al. | |
| 7,968,563 B2 * | 6/2011 | Kshirsagar et al. | 514/293 |
| 7,993,659 B2 | 8/2011 | Noelle et al. | |
| 8,017,779 B2 | 9/2011 | Merrill et al. | |
| 8,026,366 B2 | 9/2011 | Prince et al. | |
| 8,034,938 B2 | 10/2011 | Griesgraber et al. | |
| 2002/0055517 A1 | 5/2002 | Smith | |
| 2002/0058674 A1 | 5/2002 | Hedenstrom et al. | |
| 2002/0107262 A1 | 8/2002 | Lindstrom | |
| 2003/0133913 A1 | 7/2003 | Tomai et al. | |
| 2003/0139364 A1 | 7/2003 | Krieg et al. | |
| 2003/0185835 A1 | 10/2003 | Braun | |
| 2004/0014779 A1 | 1/2004 | Gorden et al. | |
| 2004/0076633 A1 | 4/2004 | Thomsen et al. | |
| 2004/0132079 A1 | 7/2004 | Gupta et al. | |
| 2004/0175336 A1 | 9/2004 | Egging et al. | |
| 2004/0180919 A1 | 9/2004 | Lee et al. | |
| 2004/0191833 A1 | 9/2004 | Fink et al. | |
| 2004/0197865 A1 | 10/2004 | Gupta et al. | |
| 2004/0202720 A1 | 10/2004 | Wightman et al. | |
| 2004/0214851 A1 | 10/2004 | Birmachu et al. | |
| 2004/0258698 A1 | 12/2004 | Wightman et al. | |
| 2004/0265351 A1 | 12/2004 | Miller et al. | |
| 2005/0009858 A1 | 1/2005 | Martinez-Colon | |
| 2005/0048072 A1 | 3/2005 | Kedl et al. | |
| 2005/0059072 A1 | 3/2005 | Birmachu et al. | |
| 2005/0070460 A1 | 3/2005 | Hammerbeck et al. | |
| 2005/0096259 A1 | 5/2005 | Tomai et al. | |
| 2005/0106300 A1 | 5/2005 | Chen et al. | |
| 2005/0158325 A1 | 7/2005 | Hammerbeck et al. | |
| 2005/0171072 A1 | 8/2005 | Tomai et al. | |
| 2005/0239735 A1 | 10/2005 | Miller et al. | |
| 2005/0245562 A1 | 11/2005 | Garcia-Echeverria et al. | |
| 2006/0045885 A1 | 3/2006 | Kedl et al. | |
| 2006/0051374 A1 | 3/2006 | Miller et al. | |
| 2006/0088542 A1 | 4/2006 | Braun | |
| 2006/0142202 A1 | 6/2006 | Alkan et al. | |
| 2006/0142235 A1 | 6/2006 | Miller et al. | |

| | | |
|---|---|---|
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0166384 A1 | 7/2007 | Zarraga |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0045886 A1 | 2/2008 | Hobbs et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | |
|---|---|---|
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| WO | WO 02/36592 A1 | 5/2002 |
| WO | WO 03/043572 A2 | 5/2003 |
| WO | WO 03/077944 A1 | 9/2003 |
| WO | WO 2005/003064 A2 | 1/2005 |
| WO | WO 2006/028451 | 3/2006 |
| WO | WO 20061063072 | 6/2006 |
| WO | WO 2006/121528 | 11/2006 |
| WO | WO 2007/030775 | 3/2007 |

OTHER PUBLICATIONS

Wozniak et al., "The Animation of 3-nitro-1, 5-naphthyridines by Liquid Ammonia/Potassium Permanganate. A New and Convenient Amination Method ", *Journal of the Royal Netherlands Chemical Society*, 102, pp. 511-513, Dec. 12, 1983.

Brennan at al , "Automated Bioassay of Interferons in Micro-test Plates." 78, 1953. *Biotechniques*, Jun./Jul., 78, 1983.

Bachman et al., '"Synthesis of Substituted Quinolylamines. Derivatives of 4-Amino-7-Chloroquinoline.", *J. Org. Chem.* 15, pp. 1278-1284 (1950).

Jain at al., "Chemical and Pharmacological Investigations of Some Substituted Alkylamino-3-aminopyridines. ", *J. Med. Chem.*, 11, pp.87-92 (1968).

Baranov et al., "Pyrazoies, Imidazoles, and Other 5-Membered Rings.", (1976). *Chem. Abs.* 85, 94362, (1976).

Berenyi et al, "Ring Transformation of Condensed Dihydro-astriazines. ", *J. Heterocyclic Chem.*, 18, pp. 1537-1540 (1981).

Chollet et al., "Development of a Topically Active Imiquimod Formulation. ", *Pharmeceutical Development and Technology*, 4(1), pp. 35-43 (1999).

Izumi et al., 1*H* -Imidazo[4,5-c]quincline Derivatives as Novel Potent TNF-a Suppressors: Synthesis and Structure-Activity Relationship of 1-, 2- and 4-Substituted 1*H* -imidazo[4,5-c]*Bioorganic & Medicinal Chemistry*, 11, pp 2541-2550 (2003).

Brassard et al., *J. Leukocyte Biology*, 71, 565-581 (2002).

Beutler et al., *Crit Care Med.*, 1993, 21 (10 Suppi), S423-S435.

Sambhi et al., *Proc Natl Acad Sci USA*, 1991, 88(9), 4025-4029.

Rothel et at., *Immunol Cell Biol.*, 1998, 76(2), 167-172.

Wedlock et al., *Immunol Cell Biol*. 1999, 77(1), 28-33.

* cited by examiner

AMIDE AND CARBAMATE DERIVATIVES OF N-{2-[4-AMINO-2-(ETHOXYMETHYL)-1H-IMIDAZO[4,5-C]QUINOLIN-1-YL]-1,1-DIMETHYLETHYL} METHANESULFONAMIDE AND METHODS

CROSS REFERENCE TO RELATED APPLICATIONS

This application is a National Stage Filing under 35 U.S.C. §371 of PCT International Application PCT/2006/035179 designating the United States of America, and filed Sep. 8, 2006. This application claims the benefit under 35 U.S.C. §119 of U.S. Provisional Application Ser. No. 60/715,950 filed Sep. 9, 2005, the entire contents of which are incorporated by reference herein.

BACKGROUND

Certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds have been found to be useful as immune response modifiers (IRMs), rendering them useful in the treatment of a variety of disorders.

There continues to be interest in and a need for compounds, the administration of which can give rise to modulation of the immune response, through induction of cytokine biosynthesis or other mechanisms.

SUMMARY OF THE INVENTION

It has now been found that certain amide and carbamate derivatives of N-{2-[4-amino-2-(ethoxymethyl)-1H-imidazo[4,5-c]quinolin-1-yl]-1,1-dimethylethyl}methanesulfonamide give rise to induction of cytokine biosynthesis. The present invention provides such compounds, which are of the following Formula I:

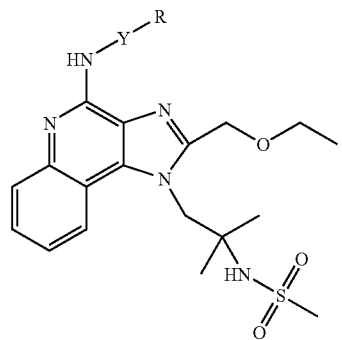

wherein R and Y are as defined below; and pharmaceutically acceptable salts thereof.

The compounds or salts of Formulas I are useful due to their ability to give rise to modulation of cytokine biosynthesis (e.g., induce the biosynthesis or production of one or more cytokines) and otherwise bring about modulation of the immune response when administered to animals. This makes the compounds useful in the treatment of a variety of conditions, such as viral diseases and neoplastic diseases, that are responsive to such changes in the immune response.

The present invention also provides pharmaceutical compositions containing the compounds of Formula and methods of inducing cytokine biosynthesis in animal cells, treating a viral disease in an animal, and/or treating a neoplastic, disease in an animal by administering to the animal one or more compounds of the Formula I, and/or pharmaceutically acceptable salts thereof or administering to the animal a pharmaceutical compostion containing one or more compounds of the Formula I, and/or pharmaceutically acceptable salts thereof.

In another aspect, the invention provides methods of synthesizing the compounds of Formula I.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments; Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula I:

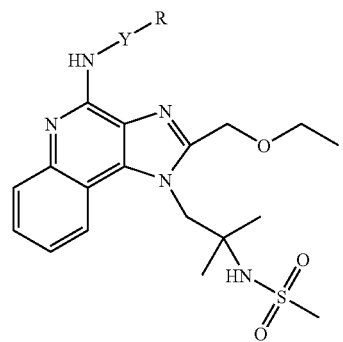

wherein R and Y are as defined below; and pharmaceutically acceptable salts thereof.

In one embodiment, the present invention provides a compound of the following Formula I:

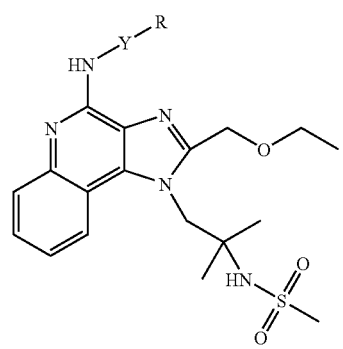

wherein:

Y is selected from the group consisting of —C(O)— and —C(O)—O—; and

R is selected from the group consisting of alkyl, aryl, arylalkylenyl, heteroaryl, heteroarylalkylenyl, heterocyclyl, and heterocyclylalkylenyl; wherein aryl and arylalkylenyl are unsubstituted or substituted by one or more substituents selected from the group consisting of alkyl, alkoxy, aryl, and halogen; and wherein the atom in heterocyclyl attached to Y is a carbon atom;

or a pharmaceutically acceptable salt thereof.

For any of the compounds presented herein, each one of the following variables (e.g., R and Y) in any of its embodiments can be combined with any one or more of the other variables in any of their embodiments and associated with Formula I, as would be understood by one of skill in the art. Each of the resulting combinations of variables is an embodiment of the present invention.

For certain embodiments, e.g., of Formula I, Y is selected from the group consisting of —C(O)— and —C(O)—O—.

For certain embodiments, e.g., of Formula I, Y is —C(O)—.

For certain embodiments, e.g., of Formula I, Y is —C(O)—O—.

For certain embodiments, including any one of the above embodiments of Formula I, R is selected from the group consisting of alkyl, aryl, arylalkylenyl, heteroaryl, heteroarylalkylenyl, heterocyclyl, and heterocyclylalkylenyl; wherein aryl and arylalkylenyl are unsubstituted or substituted by one or more substituents selected from the group consisting of alkyl, alkoxy, aryl, and halogen; and wherein the atom in heterocyclyl attached to Y is a carbon atom.

For certain embodiments, including any one of the above embodiments of Formula I, R is alkyl, aryl, or arylalkylenyl. For certain of these embodiments, R is $C_{1-10}$ alkyl. For certain of these embodiments, R is $C_{1-5}$ alkyl. For certain of these embodiments, R is selected from the group consisting of methyl, ethyl, n-propyl, isopropyl, n-butyl, isobutyl, and tert-butyl.

For certain embodiments, including any one of the above embodiments of Formula I, where not excluded, R is aryl. For certain of these embodiments, R is phenyl.

For certain embodiments, including any one of the above embodiments of Formula I, where not excluded, R is arylalkylenyl. For certain of these embodiments, R is benzyl.

For certain embodiments, the present invention provides a pharmaceutical composition comprising a therapeutically effective amount of a compound or salt of any one of the above embodiments of Formula I, and a pharmaceutically acceptable carrier.

For certain embodiments, the present invention provides a method of inducing cytokine biosynthesis in an animal comprising administering an effective amount of a compound or salt of any one of the above embodiments of Formula I, or a pharmaceutical composition comprising a therapeutically effective amount of a compound or salt of any one of the above embodiments of Formula I, to the animal.

For certain embodiments, the present invention provides a method of treating a viral disease in an animal comprising administering a therapeutically effective amount of a compound or salt of any one of the above embodiments of Formula I, or a pharmaceutical composition comprising a therapeutically effective amount of a compound or salt of any one of the above embodiments of Formula I, to the animal.

For certain embodiments, the present invention provides a method of treating a neoplastic disease in an animal comprising administering a therapeutically effective amount of a compound or salt of any one of the above embodiments of Formula I, or a pharmaceutical composition comprising a therapeutically effective amount of a compound or salt of any one of the above embodiments of Formula I, to the animal.

As used herein, the terms "alkyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene," is the divalent forms of the "alkyl" groups defined above. The term "allylenyl" is used when "alkylene" is substituted. For example, an arylalkylenyl group comprises an "alkylene" moiety to which an aryl group is attached.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and Spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom unless otherwise specified.

The invention is inclusive of the compounds described herein (including intermediates) in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic and scalemic mixtures of the enantiomers. It should be understood that the term "compound" includes any or all of such forms, whether explicitly stated or not (although at times, "salts" are explicitly stated).

Preparation of the Compounds

Compounds of the invention may be synthesized by synthetic routes that include processes analogous to those well known in the chemical arts, particularly in light of the description contained herein. The reagents are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention. For more detailed description of the individual reaction steps, see the EXAMPLES section below. Those skilled in the art will appreciate that other synthetic routes may be, used to synthesize the compounds of the invention.

Conventional methods and techniques of separation and purification can be used to isolate compounds of the invention, as well as various, pharmaceutically acceptable salts thereof. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I wherein R is as defined above. In Reaction Scheme I the 1H-imidazo[4,5-c]quinolin-4-amine of Formula II is reacted with an acid anhydride of Formula III to provide a N-(1H-imidazo[4,5-c]quinolin-4-yl)amide of Formula IV which is a subgenus of Formula I. The reaction is carried out by combining the 1H-imidazo[4,5-c]quinolin-4-amine of Formula II with an acid anhydride of Formula III in a suitable solvent such as N,N-dimethylformamide optionally in the presence of a base such as triethylamine. The reaction can be carried out at ambient temperature and the product or a pharmaceutically acceptable salt thereof can be isolated using conventional methods. The 1H-imidazo[4,5-c]quinolin-4-amine of Formula II is known and can be prepared using known synthetic methods, see U.S. Pat. No. 6,677,349 and the documents cited therein.

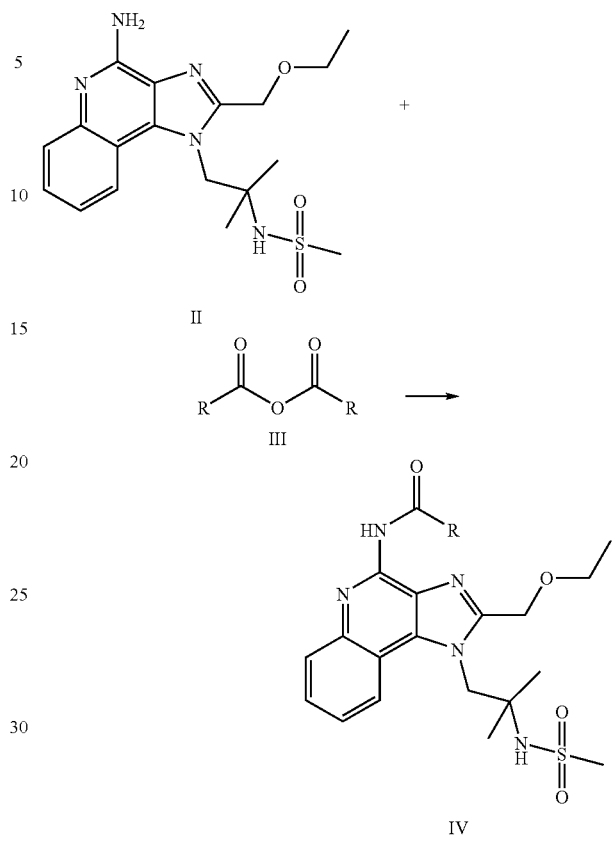

Reaction Scheme I

Compounds of the invention can be prepared according to Reaction Scheme II wherein R is as defined above. In Reaction Scheme II the 1H-imidazo[4,5-c]quinolin-4-amine of Formula II is reacted with a chloroformate of Formula V to provide a 1H-imidazo[4,5-c]quinolin-4-ylcarbamate of Formula. VI which is a subgenus of Formula I. The reaction is carried out by adding a chloroformate of Formula V in a controlled fashion to a suspension or solution of the 1H-imidazo[4,5-c]quinolin-4-amine of Formula II in a suitable solvent such as dichloromethane in the presence of a base such as triethylamine. The addition can be carried out at a sub-ambient temperature, such as for example 0° C. The product or a pharmaceutically acceptable salt thereof can be isolated using conventional methods.

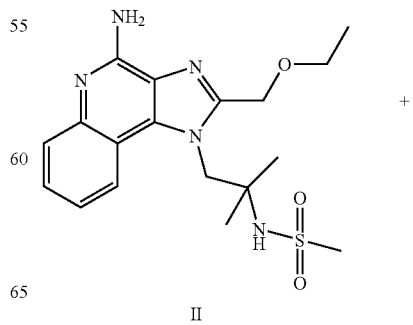

Reaction Scheme II

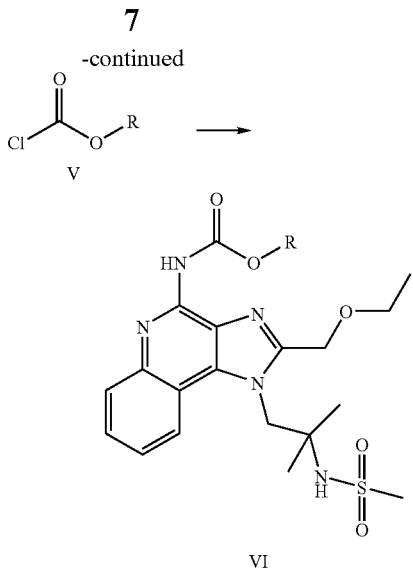

Compounds of the invention can be prepared according to Reaction Scheme III wherein R is as defined above. In Reaction Scheme III the 1H-imidazo[4,5-c]quinolin-4-amine of Formula II is reacted with an acid chloride of Formula. VII to provide a N-(1H-imidazo[4,5-c]quinolin-4-yl) amide of Formula IV which is a subgenus of Formula I. The reaction is carried out by combining the 1H-imidazo[4,5-c]quinolin-4-amine of Formula II with an acid chloride of Formula VII in a suitable solvent such as dichloromethane or N,N-dimethylformamide in the presence of a base such as triethylamine. The reaction can be carried out at ambient temperature and the product or a pharmaceutically acceptable salt thereof can be isolated using conventional methods.

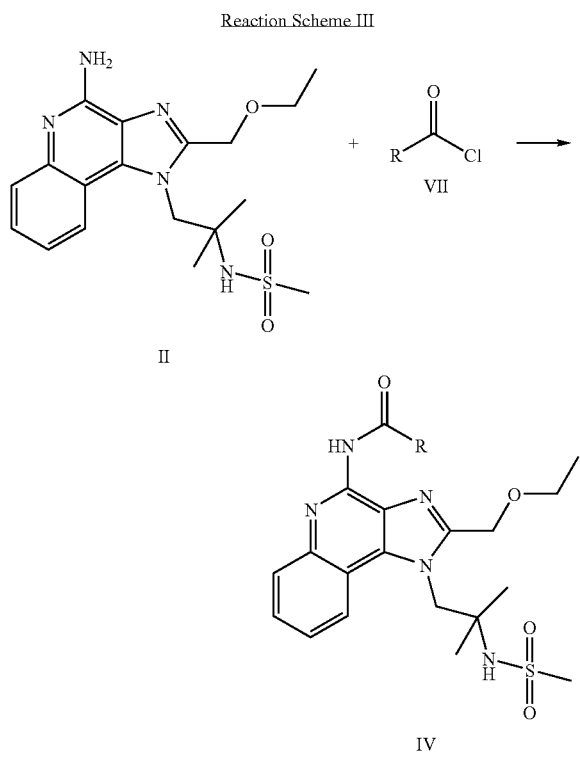

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: $m^2 = (wt\ kg^{0.425} \times height\ cm^{0.725}) \times 0.007184$, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytoldnes, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived; fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m² to about 5.0 mg/m², (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m² to about 20 mg/m² to the subject, for example, a dose of from about 0.4 mg/m² to about 1.2 mg/m².

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m² to about 5.0 mg/m², (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m² to about 2.0 mg/m² to the subject, for example, a dose of from about 0.4 mg/m² to about 1.2 mg/m².

Thus, one or more of the above diseases or types of diseases, for example, a viral disease or a neoplastic disease may be treated in an animal in need thereof (having the disease) by administering a therapeutically effective amount of a compound or salt of Formula I, any of the embodiments described herein, or a combination thereof to the animal. An animal may also be vaccinated by administering an effective amount of a compound or salt of Formula I, any of the embodiments described herein, or a combination thereof to the animal as a vaccine adjuvant. In one embodiment, there is provided a method of vaccinating an animal comprising administering an effective amount of a compound or salt described herein to the animal as a vaccine adjuvant.

The methods of the invention may be performed on any suitable subject. Suitable subjects include but are not limited to animals such as but not limited to humans, non-human primates, rodents, dogs, cats, horses, pigs, sheep, goats, or cows.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below automated flash chromatography was carried out using a COMBIFLASH system (an automated high-performance flash purification product available from Teledyne Isco, Inc., Lincoln, Nebr., USA) or a HORIZON HPFC system (an automated high-performance flash purification product available from Biotage, Inc, Charlottesville, Va., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

N-(2-Ethoxymethyl-1-{2-methyl-2-[(methylsulfonyl)amino]propyl}-1H-imidazo[4,5-c]quinolin-4-yl)acetamide

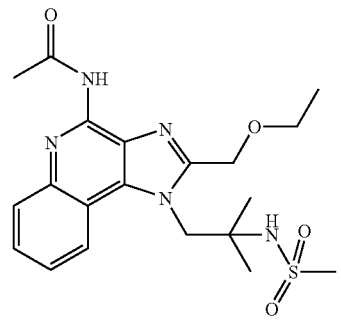 [SMILES: CCOCc1nc2c(NC(C)=O)nc3ccccc3c2n1CC(C)(C)NS(C)(=O)=O]

Acetyl chloride (150 µL, 1.1 equivalents (eq)) was added to N-{2-[4-amino-2-ethoxymethyl-1H-imidazo[4,5-c]quinolin-1-yl]-1,1-dimethylethyl}methanesulfonamide (750 mg, 1 eq) in a mixture of triethylamine (401 µL, 1.5 eq) and N,N-dimethylformamide (DMF) (5 mL) and the resulting solution was stirred at ambient temperature. After 2 hours acetic anhydride (1 mL) was added. The reaction mixture was stirred at ambient temperature for 1 hour and then concentrated under reduced pressure. The residue was purified by automated flash chromatography (silica gel eluted with a gradient of 0-10% methanol in dichloromethane containing 1% ammonium hydroxide) to provide 278 mg of N-(2-ethoxymethyl-1-{2-methyl-2-[(methylsulfonyl)amino]propyl}-1H-imidazo[4,5-c]quinolin-4-yl)acetamide as a white powder, mp 75-76° C. Anal. calcd for $C_{20}H_{27}N_5O_4S \cdot 0.40H_2O$: C, 54.50; H, 6.36; N, 15.89. Found: C, 54.70; H, 6.10; N, 15.58.

Example 2

N-(2-Ethoxymethyl-1-{2-methyl-2-[(methylsulfonyl)amino]propyl}-1H-imidazo[4,5-c]quinolin-4-yl)benzamide

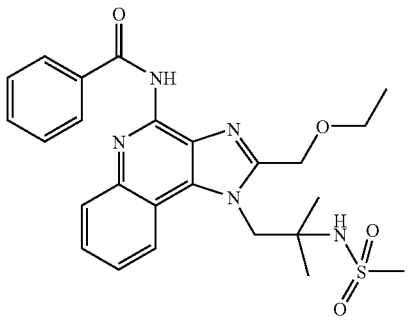 [SMILES: CCOCc1nc2c(NC(=O)c3ccccc3)nc3ccccc3c2n1CC(C)(C)NS(C)(=O)=O]

Benzoic anhydride (636 mg, 1.1 eq) was added to N-{2-[4-amino-2-ethoxymethyl-1H-imidazo[4,5-c]quinolin-1-yl]-1,1-dimethylethyl}methanesulfonamide (1 g, 1 eq) in a mixture of triethylamine (533 µL, 1.5 eq) and DMF (5 mL) and the resulting solution was stirred at ambient temperature. After 4 hours additional benzoic anhydride (about 0.1 eq) was added and the reaction mixture was stirred overnight. The reaction mixture was diluted with water (about 40 mL). The resulting suspension was adjusted to pH 7 with aqueous saturated sodium bicarbonate and then it was extracted with ethyl acetate and dichloromethane. The combined organics were concentrated under reduced pressure. The residue was purified by automated flash chromatography (silica gel eluted with a gradient of 0-10% methanol in dichloromethane containing 1% ammonium hydroxide) to provide 894 mg of N-(2-ethoxymethyl-1-{2-methyl-2-[(methylsulfonyl)amino]propyl}-1H-imidazo[4,5-c]quinolin-4-yl)benzamide as a white powder, mp 80-83° C. Anal. calcd for $C_{25}H_{29}N_5O_4S \cdot 0.60\ CH_4O$: C, 59.73; H, 6.15; N, 13.06. Found: C, 59.44; H, 5.75; N, 13.69.

Example 3

N-(2-Ethoxymethyl-1-{2-methyl-2-[methylsulfonyl)amino]propyl}-1H-imidazo[4,5-c]quinolin-4-yl)-2-methylpropanamide

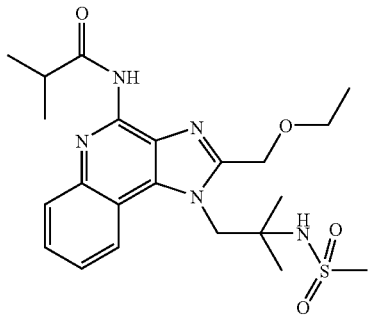 [SMILES: CCOCc1nc2c(NC(=O)C(C)C)nc3ccccc3c2n1CC(C)(C)NS(C)(=O)=O]

Isobutyric anhydride (459 µL, 1 eq) was added to N-{2-[4-amino-2-ethoxymethyl-1H-imidazo[4,5-c]quinolin-1-yl]-1,1-dimethylethyl}methanesulfonamide (1.08 g, 1 eq) in DMF (3 mL) and the resulting solution was stirred at ambient temperature. After 4 hours additional isobutyric anhydride (about 0.5 eq) was added and the reaction mixture was stirred overnight. The reaction mixture was diluted with diethyl ether (about 25 mL), stirred for 15 minutes, and then concentrated under reduced pressure. The residue was diluted with water (about 30 mL) and then extracted with ethyl acetate. The organic layer was washed with water, dried over magnesium sulfate, filtered, and then concentrated under reduced pressure to provide an oil. The oil was purified by automated flash chromatography (silica gel eluted with a gradient of 0-10% methanol in dichloromethane containing 1% ammonium hydroxide) to provide 0.77 g of a yellow powder. This material was dried under vacuum at 60° C. overnight to provide N-(2-ethoxymethyl-1-{2-methyl-2[(methylsulfonyl)amino]propyl}-1H-imidázo[4,5-c]quinolin-4-yl)-2-methylpropanamide as a yellow powder, mp 67-70° C. Anal calcd for $C_{22}H_{31}N_5O_4S \cdot 0.60H_2O$: C, 55.94; H, 6.87; N, 14.83. Found: C, 55.70; H, 6.57; N, 14.49.

Example 4

N-(2-(Ethoxymethyl)-1-{2-methyl-2-[(methylsulfonyl)amino]propyl}-1H-imidazo[4,5-c]quinolin-4-yl)-2,2-dimethylpropanamide

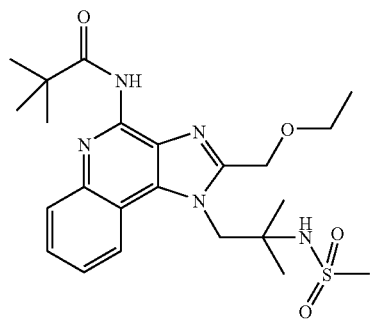 [SMILES: CCOCc1nc2c(NC(=O)C(C)(C)C)nc3ccccc3c2n1CC(C)(C)NS(C)(=O)=O]

Trimethylacetic anhydride (564 µL 1 eq) was added to N-{2-[4-amino-2-ethoxymethyl-1H-imidazo[4,5-c]quinolin-1-yl]-1,1-dimethylethyl}methanesulfonamide (1.08 g, 1 eq) in DMF (3 mL) and the resulting solution was stirred at ambient temperature. After 4 hours additional triemethylacetic anhydride (about 0.5 eq) was added and the reaction mixture was stirred overnight. The reaction mixture was diluted with diethyl ether (about 25 mL), stirred for 15 minutes, and then concentrated under reduced pressure. The residue was diluted with water (about 30 mL) and then extracted with ethyl acetate. The organic layer was washed with water, dried over magnesium sulfate, filtered, and then concentrated under reduced pressure to provide a yellow solid. The solid was purified by automated flash chromatography (silica gel eluted with a gradient of 0-10% methanol in dichloromethane containing 1% ammonium hydroxide) to provide 0.89 g of a yellow powder. This material was dried under vacuum at 60° C. overnight to provide N-(2-(ethoxymethyl)-1-{2-methyl-2-[(methylsulfonyl)amino]propyl}-1H-imidazo[4,5-c]quinolin-4-yl)-2,2-dimethylpropanamide as a yellow powder, nap 85-89° C. Anal calcd for $C_{23}H_{33}N_5O_4S \cdot 0.50H_2O$: C, 57.00; H, 7.07; N, 14.45. Found: C, 57.34; H, 6.89; N, 14.24.

Example 5

Ethyl 2-Ethoxymethyl-1-{2-methyl-2-[(methylsulfonyl)amino]propyl}-1H-imidazo[4,5-c]quinolin-4-ylcarbamate

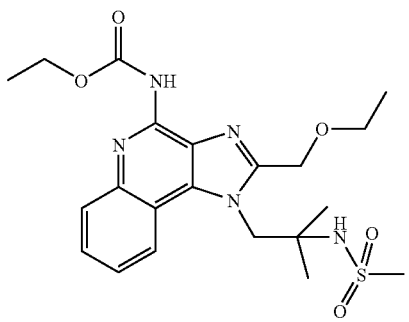 [SMILES: CCOCc1nc2c(NC(=O)OCC)nc3ccccc3c2n1CC(C)(C)NS(C)(=O)=O]

Triethylamine (2.67 mL, 5 eq) was added to a chilled (ice/water bath) suspension of N-{2-[4-amino-2-ethoxymethyl-1H-imidazo[4,5-c]quinolin-1-yl]-1,1-dimethylethyl}methanesulfonamide (1.5 g, 1 eq) in dichloromethane (150 mL). A solution of ethyl chloroformate (1.37 g, 3.3 eq) in dichloromethane (5 mL) was added dropwise to give a clear solution. The reaction mixture was allowed to come to ambient temperature with stirring for 24 hours. The reaction mixture was washed sequentially with water (150 mL), 4% sodium carbonate (150 mL), water (150 mL), and brine (150 mL). The organic layer was concentrated under reduced pressure. The residue was purified by automated flash chromatography (silica gel eluted with a linear gradient of 0-20% CMA in chloroform, 1500 mL) followed by recrystallization from diethyl ether to provide 1.25 g of ethyl 2-ethoxymethyl-1-{2-methyl-2-[(methylsulfonyl)amino]propyl}-1H-imidazo[4,5-c]quinolin-4-ylarbamate as a white powder, mp 163-165° C. Anal calcd for, $C_{21}H_{29}N_5O_5S$: C, 54.41; H, 6.31; N, 15.11. Found: C, 54.52; H, 6.43; N, 14.91.

Example 6

Propyl 2-Ethoxymethyl-1-{2-methyl-2-[(methylsulfonyl)amino]propyl}-1H-imidazo[4,5-c]quinolin-4-ylcarbamate

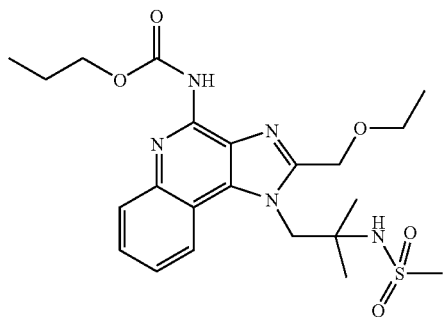 [SMILES: CCCOC(=O)Nc1nc2ccccc2c2c1nc(COCC)n2CC(C)(C)NS(C)(=O)=O]

Triethylamine (2.67 mL, 5 eq) was added to a chilled (ice/water bath) suspension of N-{2-[4-amino-2-ethoxymethyl-1H-imidazo[4,5-c]quinolin-1-yl]-1,1-dimethylethyl}methanesulfonamide (1.5 g, 1 eq) in dichloromethane (150 mL). A solution of propyl chloroformate (1.55 g, 3.3 eq) in dichloromethane (5 mL) was added dropwise to give a clear solution. The reaction mixture was allowed to come to ambient temperature with stirring for 24 hours. The reaction mixture was washed sequentially with water (150 mL), 4% sodium carbonate (150 mL), water (150 mL), and brine (150 mL). The organic layer was concentrated under reduced pressure. The residue was purified by automated flash chromatography (silica gel eluted with a linear gradient of 0-20% CMA in chloroform, 1500 mL) followed by recrystallization from diethyl ether to provide 1.23 g of propyl 2-ethoxymethyl-1-{2-methyl-2-[(methylsulfonyl)amino]propyl}-1H-imidazo[4,5-c]quinolin-4-ylcarbamate as a white powder, mp 177-179° C. Anal calcd for $C_{22}H_{31}N_5O_5S$: C, 55.33; H, 6.54; N, 14.66. Found: C, 55.41; H, 6.47; N, 14.45.

Example 7

Butyl 2-Ethoxymethyl-1-{2-methyl-2-[(methylsulfonyl)amino]propyl}-1H-imidazo[4,5-c]quinolin-4-ylcarbamate

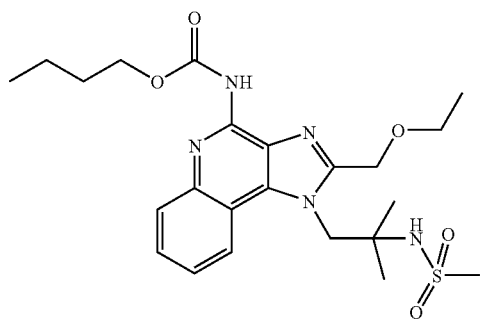 [SMILES: CCCCOC(=O)Nc1nc2ccccc2c2c1nc(COCC)n2CC(C)(C)NS(C)(=O)=O]

Triethylamine (2.67 mL, 5 eq) was added to a chilled (ice/water bath) suspension of N-{2-[4-amino-2-ethoxymethyl-1H-imidazo[4,5-c]quinolin-1-yl]-1,1-dimethylethyl}methanesulfonamide (1.5 g, 1 eq) in dichloromethane (150 mL). A solution of butyl chloroformate (1.73 g, 3.3 eq) in dichloromethane (5 mL) was added dropwise to give a clear solution. The reaction mixture was allowed to come to ambient temperature with stirring for 24 hours. The reaction mixture was washed sequentially with water (150 mL), 4% sodium carbonate (150 mL), water (150 mL), and brine (150 mL). The organic layer was concentrated under reduced pressure. The residue was purified by automated flash chromatography (silica gel eluted with a linear gradient of 0-20% CMA in chloroform, 1500 mL) followed by recrystallization from diethyl ether to provide 1.23 g of propyl 2-ethoxymethyl-1-{2-methyl-2-[(methylsulfonyl)amino]propyl}-1H-imidazo[4,5-c]quinolin-4-ylcarbamate as a white powder, mp 125-127° C. Anal calcd for $C_{23}H_{33}N_5O_5S$: C, 56.19; H, 6.77; N, 14.25. Found: C, 56.35; H, 6.65; N, 14.24.

Exemplary Compounds

Certain exemplary compounds, including some of those described above in the Examples, have the following Formula Ia, and a Y and an R substituent shown in the following table, wherein each line of the table is matched with Formula Ia to represent a specific embodiment of the invention.

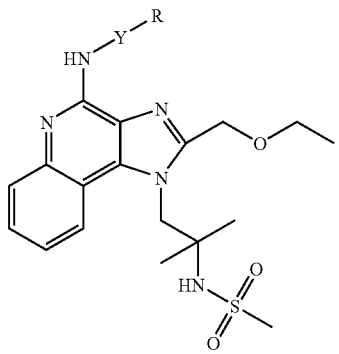

Ia

| Y | R |
|---|---|
| —C(O)— | methyl |
| —C(O)— | ethyl |
| —C(O)— | n-propyl |
| —C(O)— | isopropyl |
| —C(O)— | n-butyl |
| —C(O)— | isobutyl |
| —C(O)— | tert-butyl |
| —C(O)— | phenyl |
| —C(O)— | benzyl |
| —C(O)—O— | methyl |
| —C(O)—O— | ethyl |
| —C(O)—O— | n-propyl |
| —C(O)—O— | isopropyl |
| —C(O)—O— | n-butyl |
| —C(O)—O— | isobutyl |
| —C(O)—O— | tert-butyl |
| —C(O)—O— | phenyl |
| —C(O)—O— | benzyl |

Compounds of the invention have been found to bring about modulation of cytokine biosynthesis as shown by increased levels of interferon α and/or tumor necrosis factor α in human cells when tested using the method described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction In Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit'tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNT-μ). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula I

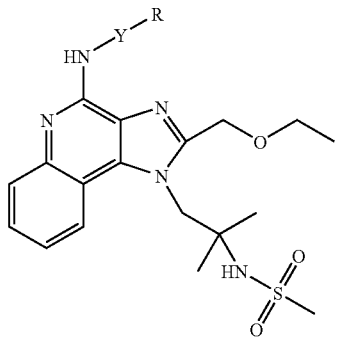

I wherein:

Y is selected from the group consisting of —C(O)— and —C(O)—O—; and

R is selected from the group consisting of alkyl, aryl, and arylalkylenyl; wherein aryl and arylalkylenyl are unsubstituted or substituted by one or more substituents selected from the group consisting of alkyl, alkoxy, aryl, and halogen or a pharmaceutically acceptable salt thereof.

2. The compound or salt of claim 1 wherein Y is —C(O)—.

3. The compound or salt of claim 1 wherein Y is —C(O)—O—.

4. The compound or salt of claim 1 wherein R is alkyl, aryl, or arylalkylenyl.

5. The compound or salt of claim 4 wherein R is $C_{1-10}$ alkyl.

6. The compound or salt of claim 5 wherein R is $C_{1-5}$ alkyl.

7. The compound or salt of claim 6 wherein R is selected from the group consisting of methyl, ethyl, n-propyl, isopropyl, n-butyl, isobutyl, and tert-butyl.

8. The compound or salt of claim 4 wherein R is aryl.

9. The compound or salt of claim 8 wherein R is phenyl.

10. The compound or salt of claim 4 wherein R is arylalkylenyl.

11. The compound or salt of claim 10 wherein R is benzyl.

12. A pharmaceutical composition comprising a therapeutically effective amount of a compound or salt of claim 1 and a pharmaceutically acceptable carrier.

13. A method of inducing the biosynthesis of at least one of interferon-alpha or tumor necrosis factor-alpha in an animal comprising administering an effective amount of a compound or salt of claim 1 to the animal.

* * * * *